United States Patent
Elverd et al.

(10) Patent No.: US 7,208,124 B2
(45) Date of Patent: Apr. 24, 2007

(54) MICROARRAYING PROCESS AND APPARATUS

(75) Inventors: David Elverd, Bournemouth (GB); James Keith Haslam, Blandford Forum (GB); Trevor Ruddock, Wimborne (GB)

(73) Assignee: Genetix Limited, Hampshire (GB)

( * ) Notice: Subject to any disclaimer, the term of this patent is extended or adjusted under 35 U.S.C. 154(b) by 488 days.

(21) Appl. No.: 10/298,948

(22) Filed: Nov. 19, 2002

(65) Prior Publication Data

US 2004/0096984 A1    May 20, 2004

(51) Int. Cl.
*B01N 3/02* (2006.01)
*G01N 1/10* (2006.01)

(52) U.S. Cl. .................. 422/100; 422/63; 422/68.1; 436/180; 73/863.32; 73/863.24; 73/863.25; 73/864; 73/864.01

(58) Field of Classification Search ................ 422/700, 422/63–67, 68.1, 100; 73/863.32, 863.24, 73/863.25, 864, 864.01; 436/180
See application file for complete search history.

(56) References Cited

U.S. PATENT DOCUMENTS

| | | | | |
|---|---|---|---|---|
| 5,508,200 A | * | 4/1996 | Tiffany et al. | 436/44 |
| 5,962,329 A | * | 10/1999 | Ershov et al. | 436/50 |
| 6,756,232 B1 | * | 6/2004 | Schermer et al. | 436/180 |
| 6,767,748 B2 | * | 7/2004 | Yokokawa et al. | 436/180 |
| 6,878,554 B1 | * | 4/2005 | Schermer et al. | 436/180 |
| 2002/0064482 A1 | | 5/2002 | Tisone et al. | |
| 2002/0142483 A1 | | 10/2002 | Yao et al. | |
| 2002/0151077 A1 | * | 10/2002 | Schermer et al. | 436/43 |
| 2002/0173048 A1 | * | 11/2002 | Nakazawa et al. | 436/180 |
| 2003/0108868 A1 | * | 6/2003 | Richards | 435/6 |
| 2003/0124735 A1 | * | 7/2003 | Nanthakumar et al. | 436/180 |
| 2004/0096367 A1 | * | 5/2004 | Schermer et al. | 422/100 |
| 2005/0118060 A1 | * | 6/2005 | Evans | 422/63 |
| 2005/0169808 A1 | * | 8/2005 | Pinkel et al. | 422/100 |
| 2005/0180892 A1 | * | 8/2005 | Davies et al. | 422/100 |

FOREIGN PATENT DOCUMENTS

| | | |
|---|---|---|
| WO | WO 02/14556 A2 | 2/2002 |
| WO | WO 02/089984 A1 | 11/2002 |

* cited by examiner

*Primary Examiner*—Brian R. Gordon
(74) *Attorney, Agent, or Firm*—Foley & Lardner LLP (57) ABSTRACT

A high throughput microarraying or colony picking robot with an automatic mechanism for exchanging pin heads and an automated washing and drying apparatus. The robot allows a dirty pin head to be deposited on the automated washing and drying apparatus for cleaning without use of the xyz-positioner, while spotting or picking can continue by picking up a clean pin head without having to wait for the dirty pin head to be cleaned. In this way, the speed of operation can be increased without any increase in the acceleration or speed of the x-, y- and z-drives. The dead time normally associated with the washing and drying cycle, which is usually several minutes, is therefore eliminated, and replaced with the much shorter dead time, of only a few tens of seconds, needed for changing between heads.

7 Claims, 13 Drawing Sheets

MICROARRAYING PROCESS AND APPARATUS

BACKGROUND OF THE INVENTION

The invention relates to a spotting and picking processes using pin heads, and to robotic apparatuses for carrying out such processes using pin heads.

Microarraying is a technique in widespread use. Conventional microarraying is based on standard multi-well plates having a 4.5 mm grid and 384 wells, although other sizes are available. Liquid samples are stored in the wells of a well plate. The liquid may be assays or any other biological or chemical sample of interest. Sub-samples of the liquid within the well plates are carried to and deposited on a spotting surface, typically microscope slides, as required. Usually many such deposits are needed and microarraying is a process whereby multiple deposits can be made simultaneously and under machine automation.

Figure 1:
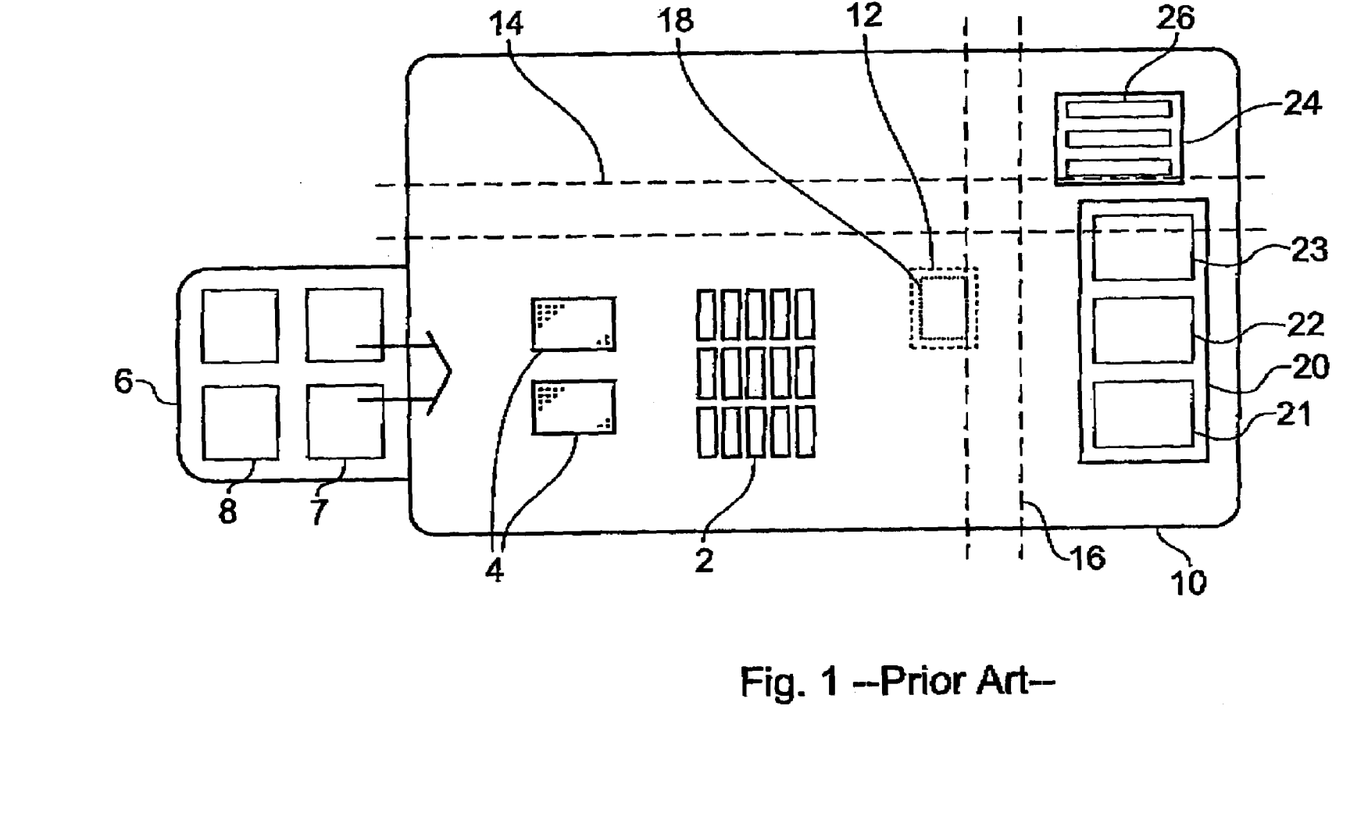
FIG. 1 is a schematic plan view of a microarraying robot according to the prior art.

FIG. 1 shows a typical microarraying robot highly schematically in plan view. The robot comprises a main bed 10 onto which well plates 4 are delivered by an automated well plate feeder 6 with a number of delivery lanes (two in the illustration) through a delidding/relidding mechanism (not shown). Each delivery lane has a feed port 7 and a restack port 8 where well plates are stacked before and after visiting the main bed 10 respectively.

The process of microarraying is one of spotting the liquid from the well plates 4 onto spotting surfaces provided by the microscope slides 2 which are also arranged on the main bed 10. This process is carried out by a pin head 12 which is moved around the robot by x- y- and z-positioners 14, 16 and 18 respectively. The pin head 12 is carried by the z-positioner, which is in turn carried by the y-positioner, which is carried by the x-positioner. These items are shown schematically with dashed lines. The pins of the pin head can be pneumatically actuated between retracted and extended positions. The process of pneumatically actuating the pins into the extended position is referred to as "firing" and is the process used to deposit liquid from the pins onto the spotting surface.

In operation, the head 12 is initially positioned so as to align its pins with the required section of one of the well plates 4. The head 12 is then actuated so as to partially immerse the pins in the liquid to be spotted. Surface tension ensures that samples of fluid remain on the pins as they are lifted away from the well plate. The pin holder is then carried by the head 12 to a chosen location above one of the microscope slides 2 for spotting where the pins are fired downwards to deposit the carried fluid at the chosen location. The liquid is deposited in a set pattern of many closely spaced spottings. One or more dense grids of spottings is usually generated by each pin. Dense spot grids, typically 11×11 squares, are generated with a 4.5 mm separation between adjacent grids.

After one round of spotting, the pin head needs to be cleaned before the pins can be used to pick up another group of samples from the well plates. For cleaning, the robot is provided with a washing station 20 and a drying station 24 which are usually arranged adjacent to each other for convenience. The washing station 20 is illustrated as including first, second and third baths 21, 22 and 23. The drying station 24 also includes halogen lamps 26 to assist drying by heating the pins.

After completion of a spotting run, the x- y- and z-positioners 14, 16 and 18 move the head over to the washing station 20. The pins are actuated into their extended positions and dipped into the first wash bath 21, containing water for example. The first bath 21 may be fitted with upstanding brushes immersed in the water, in which case the x- and y-positioners are used to move the pins over the brushes in a rotary motion in the xy-plane. The head is then moved to the second bath 22, which also contains water for further cleaning, and may also include bleach. The head is then moved to the third and last bath 23, which contains ethanol for more cleaning. Ethanol is used in the last bath 23 in view of its volatility which assists the subsequent drying of the pins. It will be appreciated that the named cleansing agents are mentioned to give concrete examples. Other cleansing agents are sometimes used.

The pin head then leaves the washing station 20 and is moved over to above the drying station 24. The halogen lamps 26 are switched on to heat the pins. An air blower is then switched on to cool the pins to ambient temperature.

The pin head 12 is now clean and ready to proceed with further spotting, so is moved over to the target well plate to pick up further liquid and the microarraying process repeats.

Colony picking uses similar apparatus to spotting, but may be considered to be the reverse process in which a pin head is used to move samples from a colony-bearing surface to a well plate. Namely, pins of a pin head are used to pick up samples from colonies and deposit them in a liquid held in wells of well plates. The colonies are provided in petri-dishes, Q-trays or omni-trays for example. Once all the pins have been used, they need to be cleaned before further inoculation to avoid cross-contamination using a similar washing and drying process to that described above for micro arraying.

The speed of picking and spotting processes is often limited significantly by the duration of the the washing and drying steps. The washing and drying steps are critical in biological applications as cross-contamination due to "carry-over" can often be a problem, so should not be compromised. The conventional way of increasing throughput of the robots is thus to increase the speed and/or acceleration of the drives used for the x- y- and z-positioners. However, this poses increased constraints upon the construction of the equipment and generally requires a disproportionate increase in cost.

SUMMARY OF THE INVENTION

The invention provides high throughput by providing a microarraying or colony picking robot with an automatic mechanism for clamping and releasing pin heads from the xyz-positioner, thereby allowing heads to be swapped, together with an automated washing and drying apparatus. This allows a dirty pin head to be deposited on the automated washing and drying apparatus for cleaning without use of the xyz-positioner, while spotting or picking can continue by picking up a clean pin head without having to wait for the dirty pin head to be cleaned. In this way, the speed of operation can be increased without any increase in the acceleration or speed of the x-, y- and z-drives. The dead time normally associated with the washing and drying cycle, which is usually several minutes, is therefore eliminated, and replaced with the much shorter dead time, of only a few tens of seconds, needed for changing between heads. Another way of considering the invention is to view it as replacing the conventional simple washing baths and drying chamber with an automated washing/drying apparatus which does not need involvement of the xyz-positioner, thereby freeing up the xyz-positioner for further spotting or picking activity.

The invention therefore provides an automated spotting or picking process, comprising: performing spotting or picking alternately between multiple pin heads, wherein spotting or picking is performed by one of the pin heads clamped to a positioning apparatus, and dirty pin heads are cleaned by depositing them into an automated washing and drying apparatus, while spotting or picking continues with another one of the pin heads clamped to the positioning apparatus.

The automated spotting or picking process uses a robot with a positioning apparatus for moving a head attached to it around the robot, wherein heads can be clamped to and released from the positioning apparatus in an automated manner by an attachment mechanism.

The process can be broken down into the following steps:
(a) performing spotting or picking using a first pin head attached to the positioning apparatus;
(b) depositing the first pin head for it to be cleaned in an automated washing and drying apparatus;
(c) picking up a second pin head that is clean;
(d) performing spotting or picking with the second pin head attached to the positioning apparatus;
(e) depositing the second pin head for it to be cleaned in the automated washing and drying apparatus;
(f) picking up the first pin head that has been cleaned in the automated washing and drying apparatus;
(g) performing spotting or picking with the first pin head attached to the positioning apparatus; and
(h) repeatedly carrying out (b) to (g).

In one embodiment, the automated washing and drying apparatus comprises first and second automated washing and drying stations. Each washing and drying station is advantageously of the same or similar construction and independently operable. Each washing and drying station has a parking bay into which a pin head can be deposited. The first automated washing and drying station can be used for washing and drying the first pin head and the second automated washing and drying station can be used for washing and drying the second pin head.

In an alternative embodiment, the automated washing and drying apparatus comprises a single automated washing and drying station. This reduces cost and complexity in the robot. If there is only one washing and drying station, additional provision needs to be made for shuffling between the clean and dirty pin heads during change over. One possibility is to provide first and second parking bays in which pin heads can be deposited, and a drive for shuttling between them so that a pin head in either parking bay can be washed and dried. A clean pin head can thus sit in one parking bay while a dirty pin head is deposited in the other parking bay. The clean pin head can then be picked up and then the dirty pin head moved across to a washing and drying position using the shuttling mechanism. (The shuttling mechanism could be activated after cleaning and before change over, instead of after change over.) Another possibility is to provide the automated washing and drying station comprises a parking bay, and the robot with at least first and second further parking bays, so that the positioning apparatus can swap a dirty pin head for a clean pin head by: (i) depositing the dirty pin head in the first further parking bay; (ii) picking up the clean pin head from the washing and drying station and depositing it in the second further parking bay; (iii) picking up the dirty pin head from the first further parking bay and depositing it in the parking bay of the automated washing an drying station; and (iv) picking up the clean pin head from the second further parking bay. However, this latter possibility is less preferred, since there are a greater number of head release and pick-up actions which results in a slower process.

According to another aspect of the invention there is provided an automated washing and drying station for a microarraying or colony picking robot, comprising:
(a) a parking bay into which a pin head can be deposited;
(b) a washing station comprising a washing area in which the pins can be washed;
(c) a drying station comprising a drying area in which the pins can be dried; and
(d) a drive for moving at least one of the parking bay, the washing station and the drying station so that a pin head parked in the parking bay can be brought together with the washing station for washing, and then together with the drying station for drying.

The automated washing and drying station preferably includes at least one inlet and outlet connected to pass cleansing liquid, typically water or a water based mixture, through the washing area. The washing area may advantageously comprise a washing chamber bounded by a top plate provided with an array of holes arranged and dimensioned to receive the pins of the pin head. The automated washing and drying may also include an air duct arranged in fluid communication with the drying area and/or at least one drying lamp, such as a halogen lamp, arranged in light communication with the drying area.

There are various possibilities for automating the washing and drying activities. The preferred solutions use a single drive only for simplicity, although there is no significant technical difficulty in using multiple drives. In the best mode, the parking bay and drying station are static and the washing station motorized. Namely, the drive is operable to move the washing station into and out of a washing position, with the parking bay and the drying station remaining static. An alternative is for the drive to move the parking bay between the washing station and the drying station.

The invention also provides a microarraying or colony picking robot comprising a positioning apparatus operable to move a pin head attached to it to perform spotting or picking and including an attachment mechanism to allow swapping between different pin heads by automated deposit and pick up, and at least one automated washing and drying station operable to clean pin heads deposited by the positioning apparatus.

BRIEF DESCRIPTION OF THE DRAWINGS

For a better understanding of the invention and to show how the same may be carried into effect reference is now made by way of example to the accompanying drawings in which.

DETAILED DESCRIPTION

Figure 2:
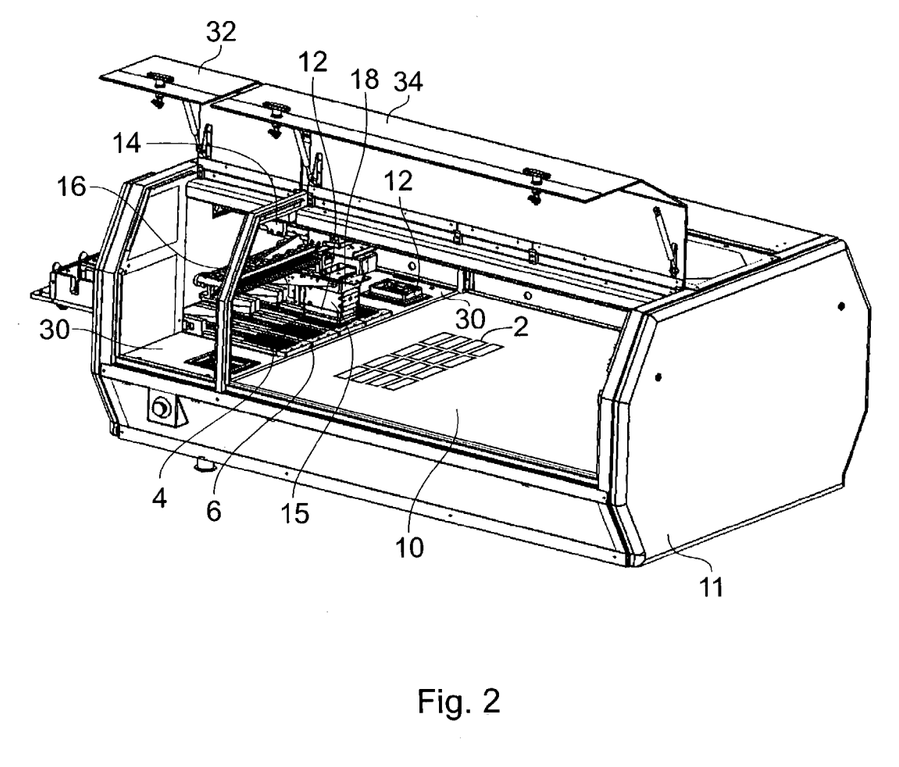
FIG. 2 is a perspective view of a microarraying robot according to an embodiment of the invention.
Figure 3:
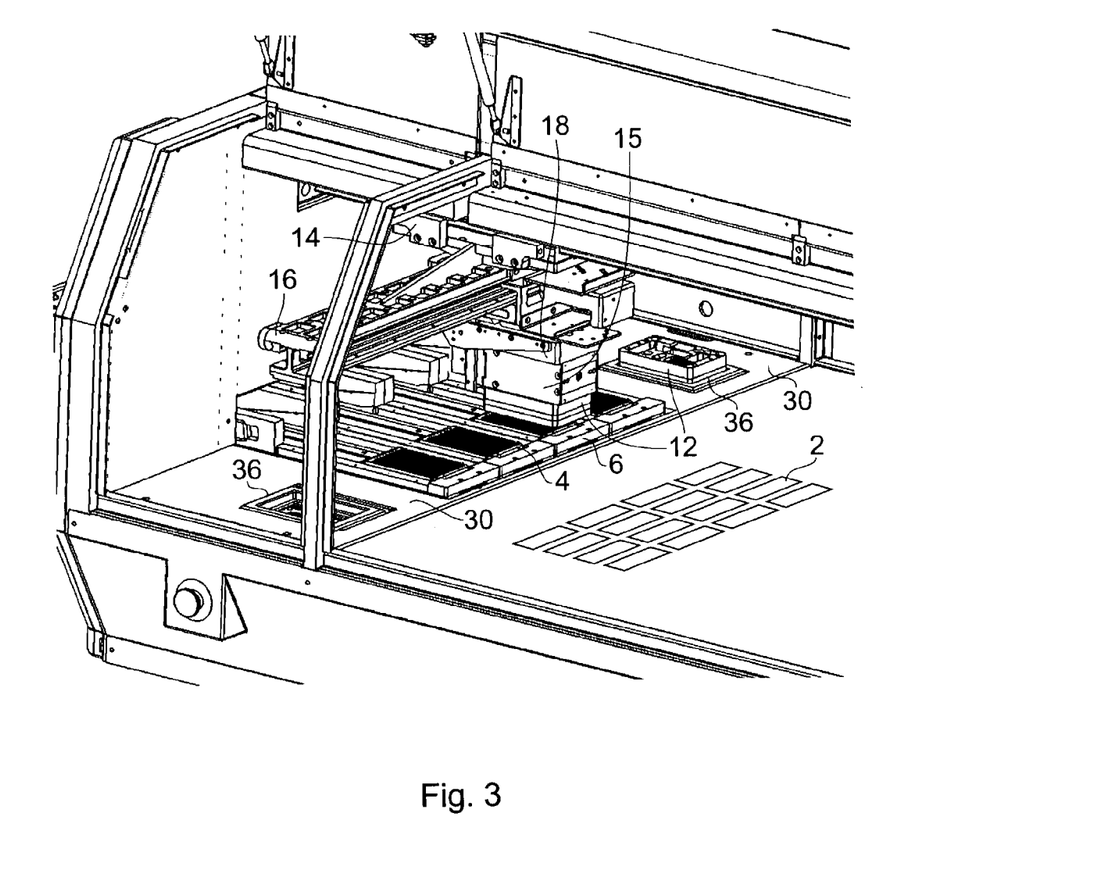
FIG. 3 is a close up of FIG. 2 showing the robot in more detail.

FIGS. 2 and 3 are perspective views of a microarraying robot according to an embodiment of the invention, with FIG. 3 being a close up of FIG. 2. The robot comprises a main bed 10 contained within a housing 11. Access to the main bed 10 is provided by doors 32 and 34. Well plates 4 are delivered to the main bed 10 of the robot by an automated well plate feeder 6 which, in the illustration, has four lanes. Each lane has a de-lidding/re-lidding mechanism 31 for removing and replacing the well plate lids as the well plates pass through. Each delivery lane is supplied from a feed port (hidden behind the end panel of the housing) to which is docked a cassette filled with well plates. Each feed port has a supply mechanism that deposits well plates, one at a time, onto the delivery lane. Behind each of the feed ports there is arranged a restack port (also hidden) which has a pneumatically driven lifting mechanism for inserting well plates returned from the main bed of the apparatus into a further cassette. On their return, the well plates pass through the feed ports before reaching the restack ports. For the sake of brevity, the mechanical design of the well plate feeder is not described further. For further details, reference is made to copending U.S. patent application Ser. No. 10/133,904, the contents of which are incorporated herein by reference. Other embodiments may not use an automated well plate feeder and instead rely on manual placement of well plates on the main bed 10.

First and second automated washing and drying stations 30 are arranged to the left of the main bed 10 either side of the well plate delivery lanes. Each washing and drying station 30 comprises a parking bay 36 into which a pin head 12 can be deposited. In the illustration, the washing and drying station 30 situated furthest away from the access doors 32 and 34 is shown with a pin head docked in the parking bay, whereas the washing and drying station 30 nearest the access doors 32 and 34 is shown empty. A second pin head 12 can be seen attached to the positioning apparatus. The positioning apparatus comprises x-, y- and z-positioners 14, 16 and 18 respectively. The z-positioner 18 has an attachment mechanism in the form of a head latching unit 15 for releasably connecting a pin head 12 to it. The z-positioner 18 is carried by the y-positioner 16, and the y-positioner 16 is carried by the z-positioner 14, as is conventional. The z-positioner 14 is largely obscured in the illustration by the roof of the housing 11. The main bed 10 has arranged thereon a number of microscope slides which provide spotting surfaces 2 onto which liquid contained in the well plates 4 can be spotted to form regular grids of spots during microarraying. It will be appreciated that any suitable spotting surface can be provided.

In operation, the head 12 held by the latching unit 15 in the Z-positioner 18 can be moved between the well plates 4 at the end of their delivery lanes and the spotting surfaces 2 in order to perform spotting. Once all the pins of the pin head are used (i.e. dirty), the dirty pin head can be deposited into the vacant parking bay 36. The dirty pin head can then be washed and dried in the automated washing and drying station 30. After depositing the dirty pin head into the vacant parking bay 36, the positioner can then move to pick up the other pin head from the parking bay 36 of the other washing and drying station 30, this pin head having been cleaned in the other washing and drying station 30. In this way, spotting is only interrupted for the short time needed to exchange heads and does not need to wait for a washing and drying cycle to complete before continuing to spot.

Having described the basic layout of the machine, the automated washing and drying station 30 is now described in detail, followed by a detailed description of the automated head attachment mechanism 15 which allows pin heads to be deposited in the parking bays and then subsequently picked up.

Figure 4:
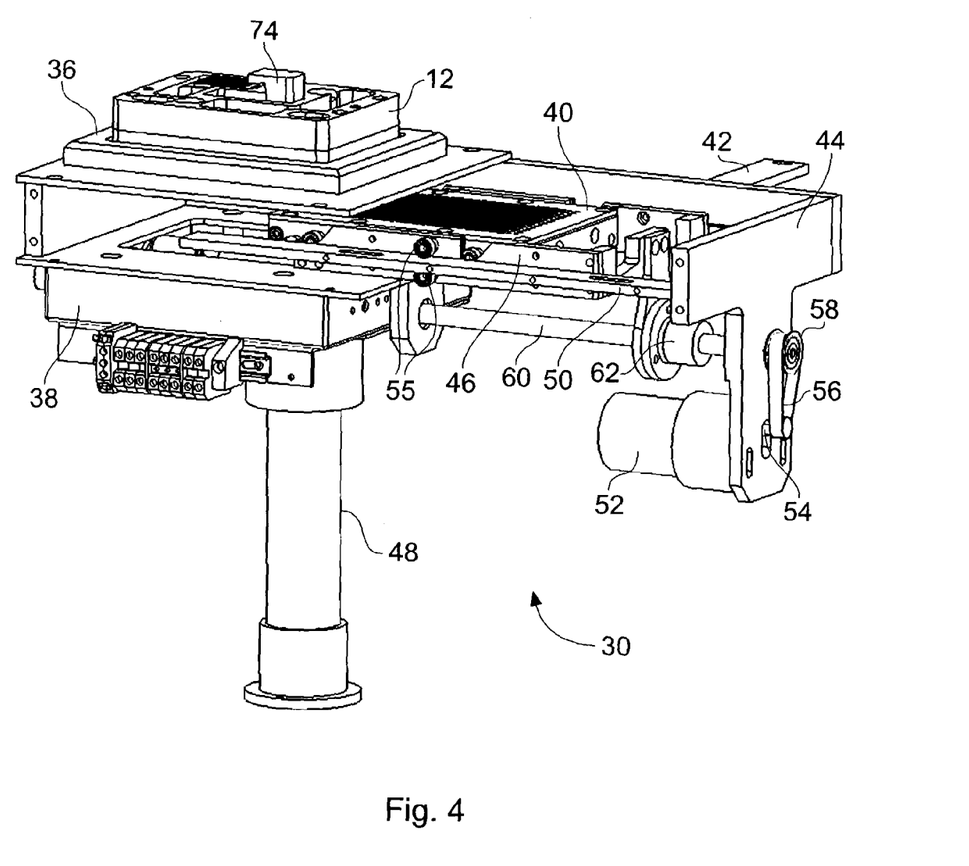
FIG. 4 is a perspective view of a combined washing/drying station.

FIG. 4 is a perspective view of one of the automated washing and drying stations 30. The washing and drying station 30 is shown with a pin head 12 lying in the parking bay 36 of the park station 37. The pin head 12 is connectable to the attachment mechanism 15 of the z-positioner using a latch shoe 74 which can be seen in the illustration. Directly below the park station 37 there is arranged a drying station 38. The drying station 38 is connected to an air duct 48 through which air is blown into the drying station to dry the pins of the pin head 12 after washing. The washing and drying station 30 is designed with static park and drying stations 37 and 38 and a mobile washing station. The washing station comprises a carriage 40 supported by a cradle 46 which is drivable between a washing position, in which the pins of the pin head are immersed in cleansing liquid held in the washing carriage 40, and a drying position, in which the washing carriage 40 and cradle 46 are withdrawn away from the parking station to allow drying of a pin head 12 held in the parking station 37 by the drying station 38.

The cradle 46 for the washing carriage 40 can travel between the washing and drying positions using pairs of guide rollers 55 which tangentially engage either side of a guidance rail 50. Motion of the cradle 46 along the guidance rail 50 is driven by an electric motor 52 which connects via a motor spindle 54, drive belt 56 and pulley 58 to a lead screw 60 that is in threaded engagement with a lead screw nut 62. The lead screw nut 62 is connected to a plate which is fixed to the cradle 46 to impart the motion of the lead screw nut 62 to the cradle 46. The various parts of the washing and drying station 30 are supported in a main frame 44 to which are attached two pairs of mounting brackets 42 which allow the washing and drying stations 30 to be secured to the underside of the main bed 10.

Figure 5:
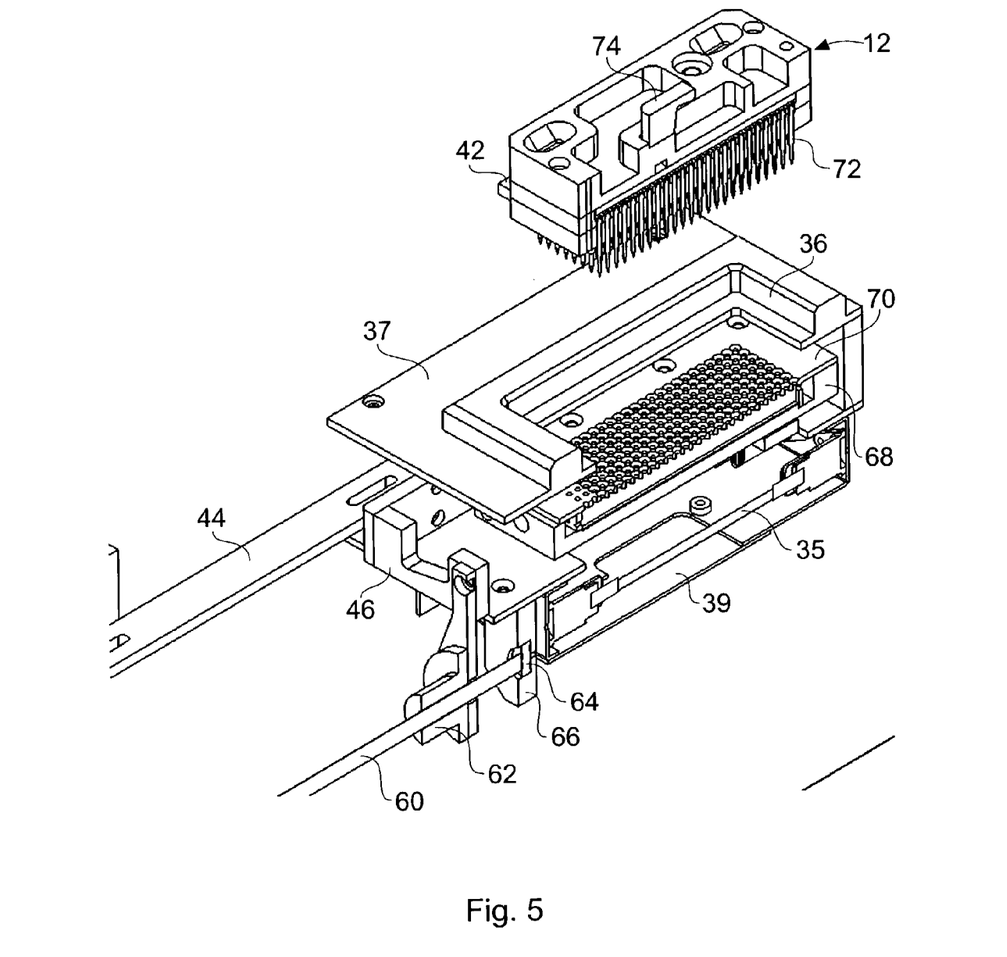
FIG. 5 is a perspective section view of one end of a combined washing/drying station with a pin head above.

FIG. 5 is a perspective section view of one end of the combined washing and drying station 30 with a pin head 12 shown vertically above the parking bay 36. The pin head 12 is also shown in the same section. The latch shoe 74 and pins 72 of the pin head 12 are evident. Various parts of the washing and drying station 30 that have already been described can be seen, namely the park station 37, parking bay 36, main frame 44, mounting bracket 42, cradle 46 and washing carriage 40. It can be seen that the washing carriage 40 comprises a main body 68 and a top plate 70. The lead screw 60 and the lead screw nut 62 are also evident. The lead screw 60 is journalled in a bearing 64 held in a bearing housing 66. Further details of the drying station are also visible. Namely, it can be seen that the drying station comprises a chamber 39 into which the air duct vents from below. Moreover, extending across the drying chamber, a number of halogen bulbs 35 are provided. The embodiment uses three halogen bulbs 35, one of which is visible in the illustration. The halogen bulbs 35 provide a light source to assist drying of the pins 72 by radiative heating. The pin temperatures can be elevated in this way up to 200° C. Air from the air duct is then used to cool the pins to bring them back to ambient temperature ready for further use. An example of a suitable halogen lamp is standard quartz 300 W linear lamps of the R7 type, e.g. Osram Haloline 64701 or Philips Plusline. In an example drying process, a pin head is illuminated for a period of 4–30 seconds after which an air blower is switched on to blow air through the air duct for a period of 5–50 seconds, for example, to allow cooling of the pins to ambient temperature.

Figure 6:
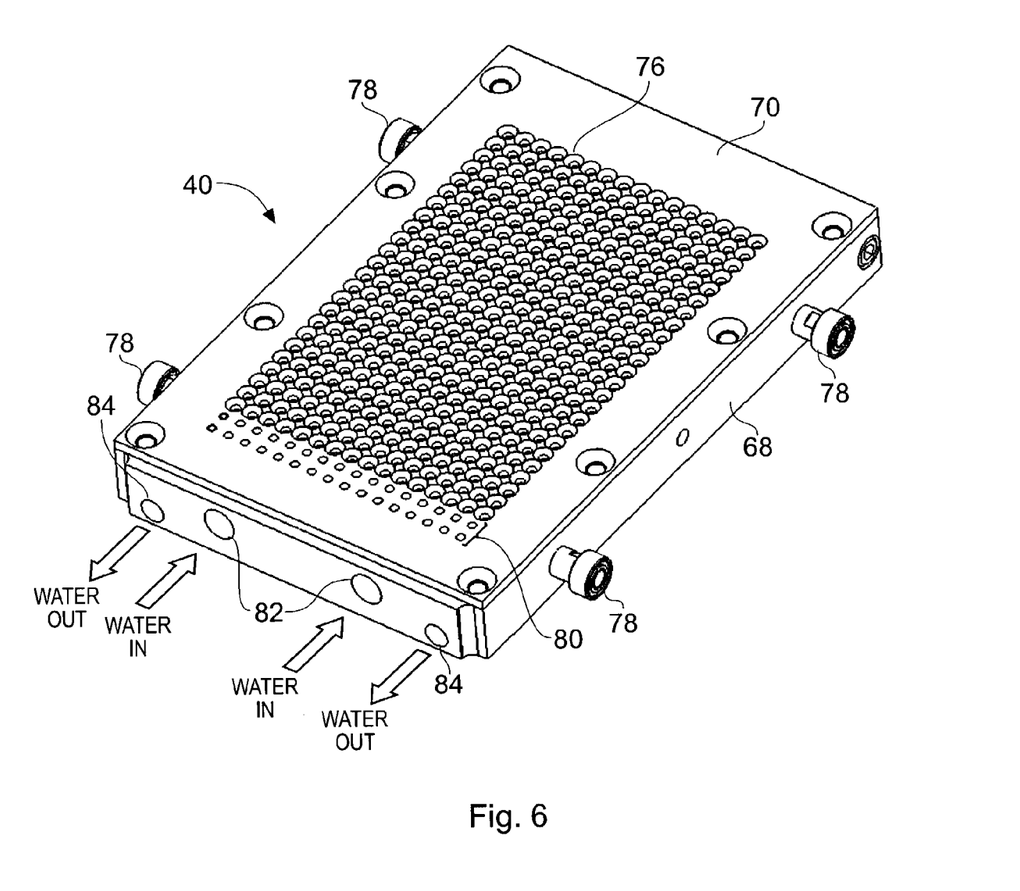
FIG. 6 is a perspective view of a wash carriage.

FIG. 6 is a perspective view of the wash carriage 40 in which its main body 68 and top plate 70 are evident. It can be seen that the top plate 70 is perforated by an array of pin holes 76 matched to the pin array of the pin head 12. It will be appreciated that the embodiment shown is for a 384-pin pin head with a 16×24 array of pins 72 conforming to the 384-well well plate standard. It will be appreciated that other standards could be catered for by simple modification. Each hole has a diameter 0.2 mm greater than the external pin diameter to allow passage of the pins 72 through the holes 76. In addition to the square-pitch array of 16×24 pin holes 76, it can be seen that a further two rows of dummy pins 80 are provided. These pins extend into the interior of the washing carriage 40. Their purpose is described further below. The wash carriage 40 has four rollers 78 which locate the carriage 40 in the cradle 46, as will be described with reference to the following figures. The main body 68 is provided at one end with a pair of liquid inlets 82 and a pair of liquid outlets 84 which provide for the circulation of water or other cleansing liquid through the wash carriage 40. Standard flexible plastic tubing is used with standard fittings to connect the inlets and outlets to suitable liquid supplies and drains.

Figure 7:
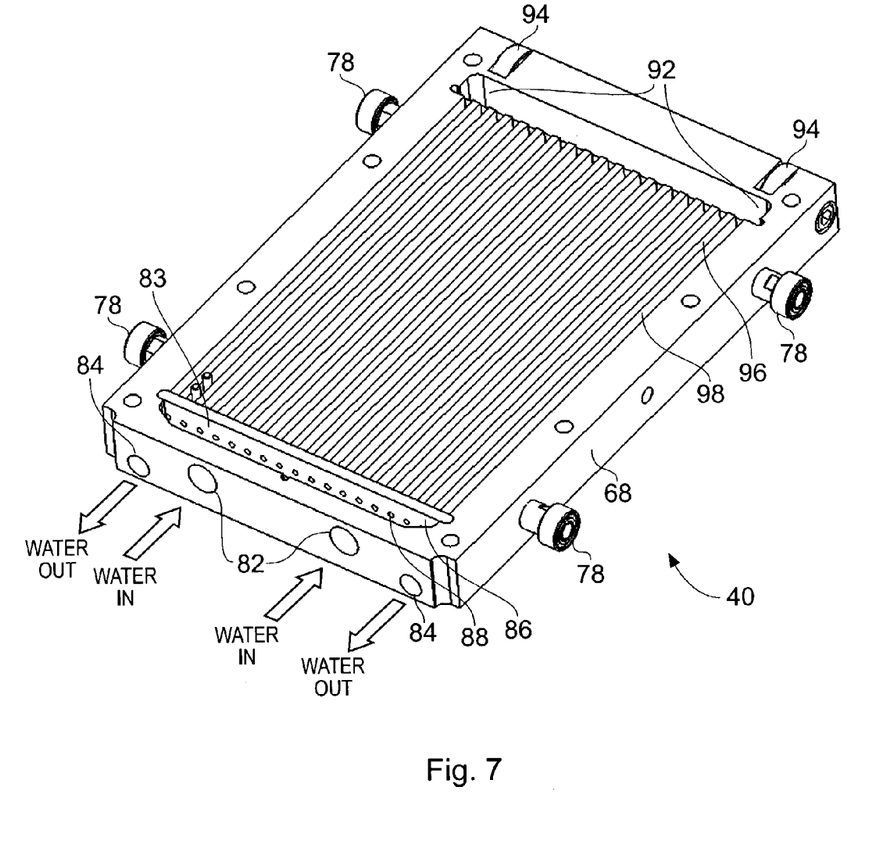
FIG. 7 shows the wash carriage of FIG. 6 with the top plate removed.

FIG. 7 shows the wash carriage again, but with the top plate 70 removed to reveal the internal construction of the main body 68 which provides for circulation of the cleansing liquid. Water injected into the washing carriage via the inlets 82 fills an entry chamber 83 bounded by a weir 86 that is perforated with holes 88. Running parallel along the washing carriage are a series of channels 98, one for each row of pins or pin holes. The channels 98 are defined by dividing walls 96 which run over the full length covered by the pin holes 76. Two of the dummy pins 80 are also illustrated by way of example. The dummy pins 80 extend into the inlet ends of the channels 98 adjacent to the weir 86 so that, when water is injected into the channels through the holes 88, the dummy pins 80 induce turbulent flow prior to the cleansing liquid reaching the first row of pins of the pin head which are held in the channels 98 during washing. This ensures that the first row of pins in the pin head is cleaned efficiently. Once water has passed along the channels 98 it reaches an end chamber 90. At each side of the end chamber 90 there is a drain hole 92 (not visible) which forms one end of a bore. Two bores thus extend along each side of the main body 68 parallel to the channels and emerge at the outlets 84, thus completing the circulation path for the cleansing liquid. As well as the carriage support rollers 78, the figure also shows a pair of end rollers 94 arranged at the opposite end of the wash carriage 40 to the water feed connections 82 and 84. The use of these end rollers 94, and also the rollers 78, is described with reference to the following figures.

FIGS. 8A–8D show section side views of the washing and drying station 30 at different positions of the washing carriage 40 as it moves into its washing position. Each of the figures shows the pin head 12 located in the parking bay 36 with its latch shoe 74 upstanding. The pins 72 of the pin head 12 are also shown and point down towards the drying chamber 39 arranged in the base of the washing and drying station 30.

Figure 8A:
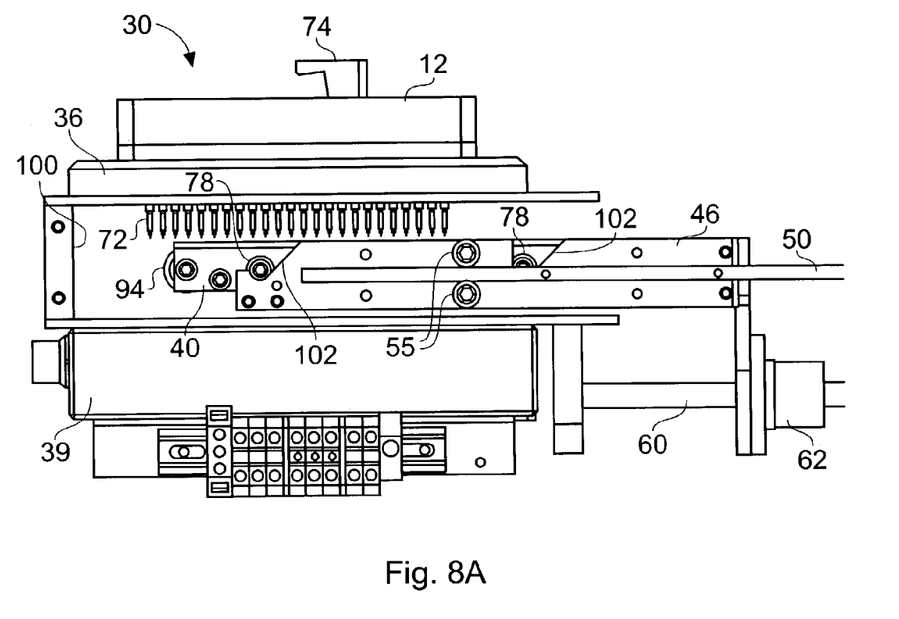
FIGS. 8A–8D show section side views of the washing/drying station for different positions of the wash carriage as it moves into its washing position, with FIG. 8A showing the wash carriage at an intermediate position of the drive midway between the washing and drying positions, FIG. 8B showing the wash carriage advanced to the furthest left abutting the end wall of the main frame, FIG. 8C showing the wash carriage moving upwards towards the pins, and FIG. 8D showing the wash carriage fully elevated in the washing position with the pins immersed in the washing chamber.

FIG. 8A shows the washing carriage is in an intermediate position of the drive, midway between the washing and drying positions. The lead screw nut 62 is thus positioned midway along the lead screw 60 and is moving the wash carriage 40 from right to left in the figure by rolling of the guide rollers 55 along the guidance rail 50. As the cradle 46 moves from right to left, the washing carriage 40 remains stationary in the cradle with the rollers 78 resting at the bottom of a pair of ramps 102. One of the end rollers 94 is also illustrated. The end rollers 94 are approaching an end wall 100 of the main frame 44 in the course of the motion.

Figure 8B:
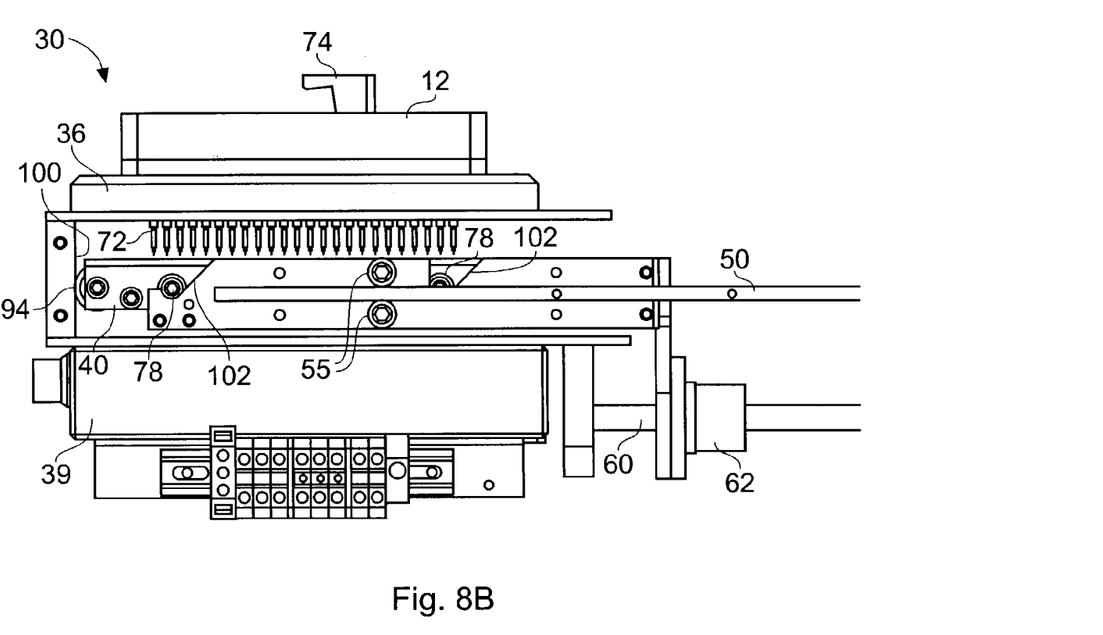

FIG. 8B shows the washing carriage 40 advanced to a position at which the end rollers 94 have just touched the end wall 100 of the main frame. From this point onwards, further actuation of the drive to move the lead screw nut 62 and thus the cradle 46 further towards the end wall 100 (i.e. to the left) results in the wash carriage rollers 78 being forced to move up the ramps 102 and also the end rollers 94 to roll vertically up the end wall 100.

Figure 8C:
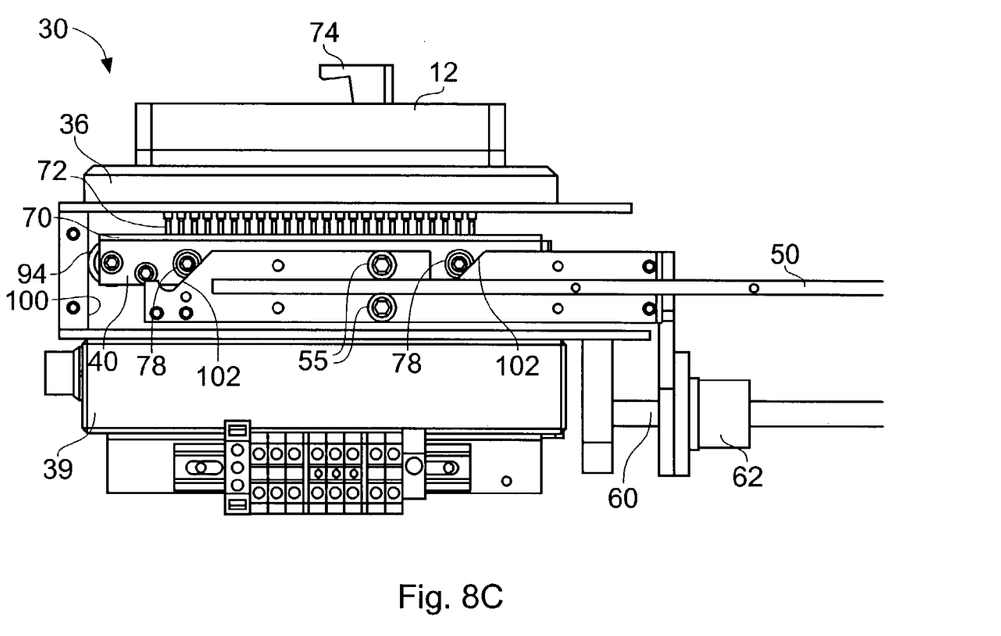

FIG. 8C shows the wash carriage 40 after it has been raised by motion of the rollers 78 part way up the ramps 102 as the cradle 46 moves further towards the end wall 100. At this point it can be seen that the ends of the pins 72 have inserted into the pin holes of the top plate 70.

Figure 8D:
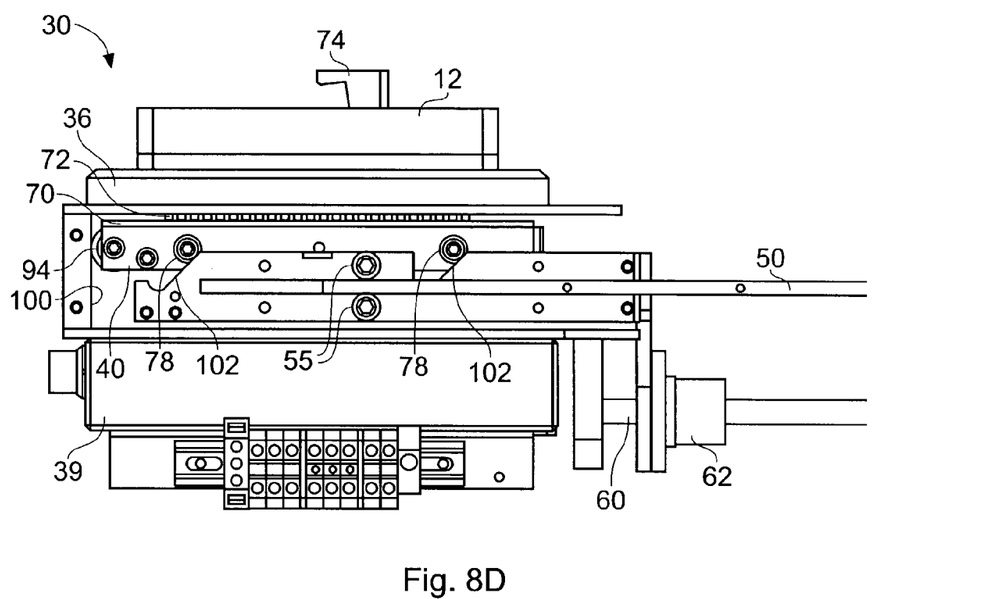

FIG. 8D shows the final stage in the motion in which the wash carriage 40 is at its maximum vertical height with the pins 72 inserted near fully into the wash carriage 40. The rollers 78 are near the top of the ramps 102 and the frame 46 is at its closest position to the end wall 100. It is noted that even at this maximum height, there is a small clearance between the bottom face of the parking bay 36 and the top plate 70 of the wash station. The position illustrated in FIG. 8D is the washing position.

It will be appreciated that the wash station is separated from the pin head using the reverse procedure to that described. Namely the wash carriage 40 is lowered by motion of the rollers 78 down the ramps 102, as induced by motor driven motion of the frame 46 away from the end wall 100. Once the rollers 78 have reached the bottom of the ramps 102, the wash carriage 40 remains static in the frame 46 and the frame 46 and carriage 40 move together away from the parking bay 36 and drying chamber 39. The frame 46 and wash carriage 40 move further to the right than shown in FIG. 8A into a drying position in which the end rollers 94 are beyond (i.e. to the right of) the drying chamber 39, thereby providing free space between the drying chamber 39 and parking bay 36 so that uninhibited drying of the pins 72 can take place.

The attachment mechanism used for automated exchange of pin heads is now described in detail.

Figure 9:
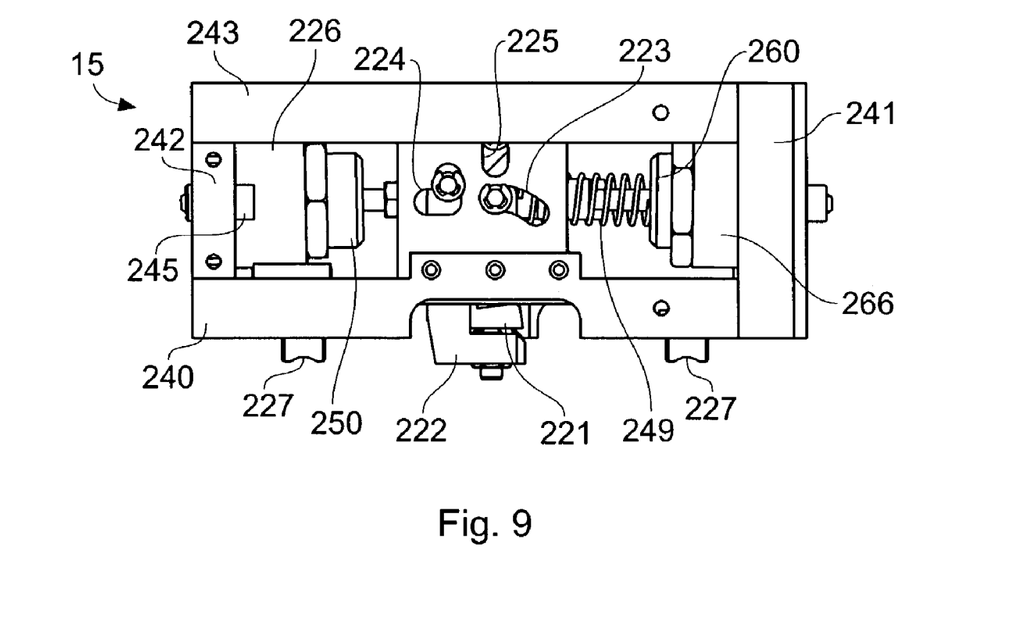
FIG. 9 is a side view of the head latching unit that is attached to the z-positioner motor drive.

FIG. 9 is a side view of the attachment mechanism which takes the form of a latching unit 220 that is attached to the z-positioner motor drive and serves to allow different pin heads to be loaded and unloaded.

Figures 10, 11:
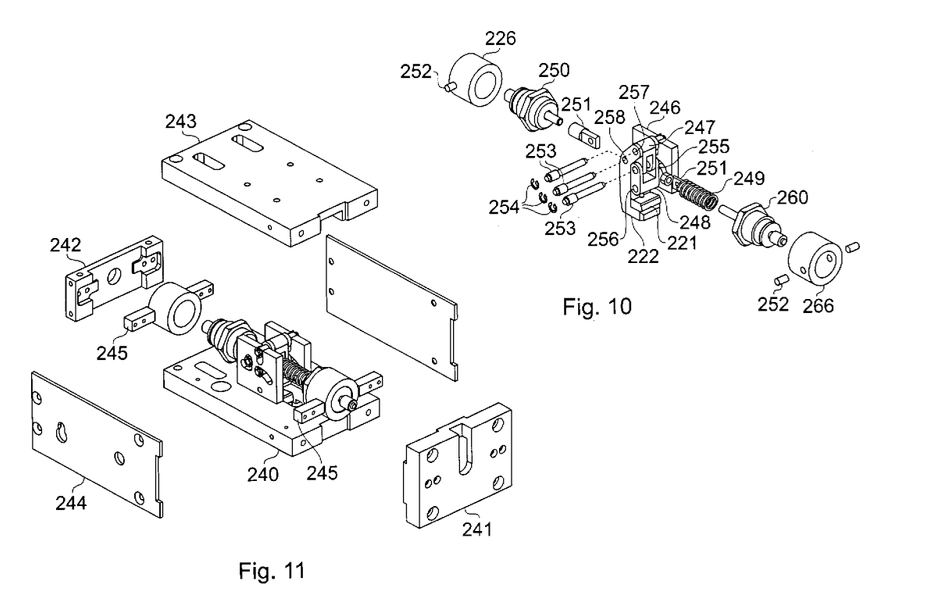
FIG. 10 is an exploded perspective view of the head latching mechanism of the head latching unit.
FIG. 11 is an exploded perspective view of the head latching unit with the head latching mechanism of FIG. 10 partly assembled.

FIG. 10 is an exploded perspective view of the head latching mechanism of the head latching unit 220.

FIG. 11 is an exploded perspective view of the head latching unit 220 with the head latching mechanism of FIG. 10 partly assembled.

The head latching unit 220 comprises a housing made of top and bottom plates 243 and 240 and left and right end plates 242 and 241. Non-structural side plates 244 are also provided (omitted from FIG. 9, but evident in FIG. 11). The bottom plate 240 is provided on its lower side with locating stubs 227 to assist location of the head latching unit in corresponding holes in the heads.

The latching mechanism is driven by a push-me-pull-you pneumatic piston assembly comprising a delatch driving piston 250 and a latch driving piston 260 with respective cylinders 226 and 266. The cylinders 226 and 266 are rotatably mounted by spigots 252 (see FIG. 10) located in blocks 245 (see FIG. 11) secured to the base plate 240 in a manner similar to a howitzer.

The cylinders act on a knee joint 255 connecting to a floating upper joint 257 by an upper link 247. The knee joint 255 is also connected to a lower fixed joint 256 by a lower link 248. The fixed joint 256 is located in the side plates 246 (only one of which is shown in FIG. 10) by a locating pin. The knee joint 255 is connected to both pistons 250, 260 by respective connectors 251 assisted by a locating pin 253. The knee joint 255 has a pin 253 running through it which fits into a pair of arcuate slots 223 in the side plates 246 retained by a pair of outside circlips 254. The floating upper joint 257 also has a pin 253 running through it which fits in a pair of vertical slots 225 in the side plates 246 retained by a pair of outside circlips 254. The floating upper joint pin also pivotally mounts a latching arm 222. The latching arm 222 extends obliquely down to a non-jointed bend 258 with a hole through which a further pin 253 passes which is retained by outside circlips 254 and fits into an L-shaped slot 224 in the side plates 246. After the non-jointed bend 258, the latching arm 22 extends vertically down and then at right angles thereto extends further to form a latch support which bears a latch 221.

Before describing the latching action by which heads are attached to and detached from the latching unit 220, the latching parts of the heads are first described.

Figure 12:
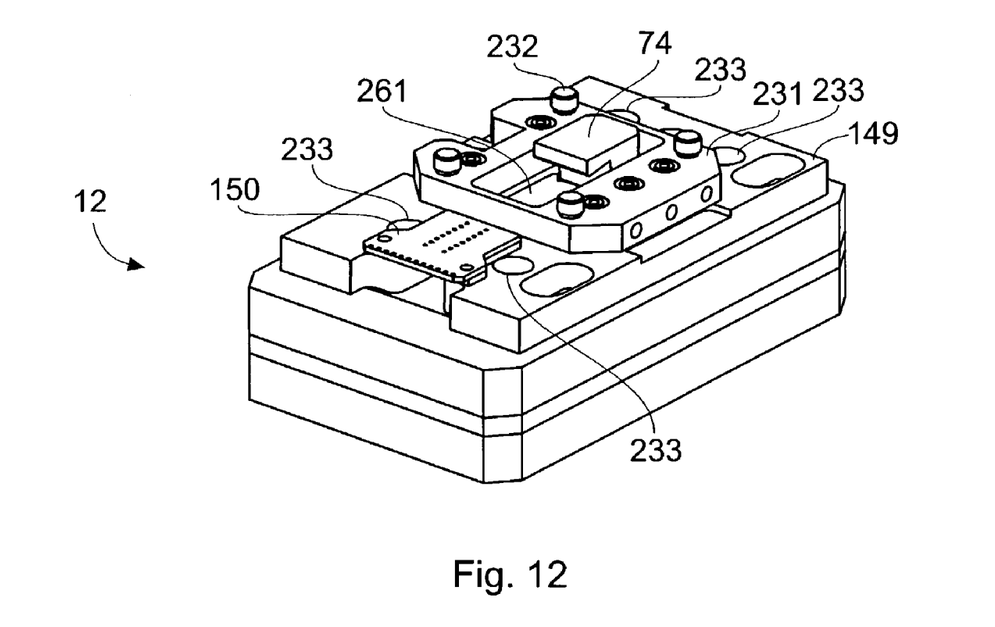
FIG. 12 is a perspective view of a pin head showing parts used to secure the head to the head securing unit.

FIG. 12 is a perspective view of a pin head 12 showing parts used to secure the head to the head securing unit. The head 12 is secured to the z-positioner via a securing plate 149 on its upper side. The securing plate 149 also provides a host for an electrical contact pad 150 which mates with a corresponding contact pad on the z-positioner. The contact pad 150 provides the head 12 with electrical power feeds for actuating valves for pneumatically firing the pins and also communication feed-throughs for providing communication lines from the main robot to logic within the head. For example each head has a unique identifier so that the robot can interrogate the head to receive identification data and thus determine the head's identity, which can be used to define the head's home parking bay, for example. It is also mentioned that each parking bay is fitted with a microswitch to communicate to the control system whether it is occupied or vacant. In this way, the system is robust against an operator removing a parked head manually for inspection and returning it to a different parking bay.

Locating holes 233 for accepting the locating stubs 227 on the head latching unit 220 can be seen. In addition there are four locating stubs 232 on the head 12 which locate in corresponding holes in the head latching unit 15 (not visible in FIGS. 9–11). The stubs 232 are mounted on a plate 231 which mounts a lower latch 74 which has a fixed position and is shaped and dimensioned to engage with the latch 221 of the head latching unit.

The latching mechanism has two basic positions, a latched position, in which the head is gripped by the latch and securely engaged with the head latching unit 15, and a delatched pre-engagement position. FIGS. 9–11 illustrate the mechanism in the latched position. In view of this, movement of the mechanism from the latched position to the delatched position is described. This is the movement that would be performed when a head had been returned to its parking bay and was to be released by the head latching unit to allow the z-positioner with head latching unit to be moved away to pick up a different head.

Referring to FIG. 9, the delatching piston 250 is pneumatically actuated by compressed air through a feed line (not shown) which pushes the knee joint 255 to the right (as viewed in the figures) which pushes the pin around the arcuate slot 223. This forces the floating upper joint 257 vertically down guided and constrained by the vertical slot 225. Initially, the non-jointed bend 258 is also forced vertically down guided by the upright part of the L-shaped slot 224. During this phase of the delatching, the latch 221 is being moved vertically down, allowing it to become free of the head's latch 74 (assuming the head 12 is supported in its parking bay). Once the downward motion proceeds to the point at which the base of the L-shaped slot has been reached by the non jointed bend 258 of the latching arm 222, the latching arm 222 is forced to rotate by the pin through the non-jointed bend 258 being confined to move in the base of the L-shaped slot until it abuts the end of the base section of the L-shaped slot. The mechanism is now in the delatched position, with the knee joint 255 at its maximum bend and the latching arm 222 at is maximum swing angle away from vertical, swung into a space 261 provided within the plate 231. At this point, the latching arm 222 has swung away sufficiently to allow the latching unit 15 to be lifted away from the head 12 by a simple vertical motion of the z-positioner. It will now be appreciated why the piston assemblies are pivotally mounted, namely to accommodate movement of the pins in the slots 223, 224 and 225.

Motion from the delatched to the latched position proceeds approximately in the reverse sequence. It is initiated by actuation of the latching piston 260 which acts on the knee joint 255 to straighten it out. The reverse sequence of slot motion is performed in relation to the latch-to-delatch motion with the latching arm 222 being forced to move vertically upward in the L-shaped slot 224 when the pin through the non-jointed bend 258 reaches the corner of the L-shaped slot 224. Worthy of mention is the fact that it in the final stages of straightening when moving into the latched position, the design allows a high amount of clamping force to be exerted, with the head's latch 74 being squeezed between the latching unit's latch 221 and the bottom of the lower link 248. This feature provides a highly secure latching of the head.

Figure 13:
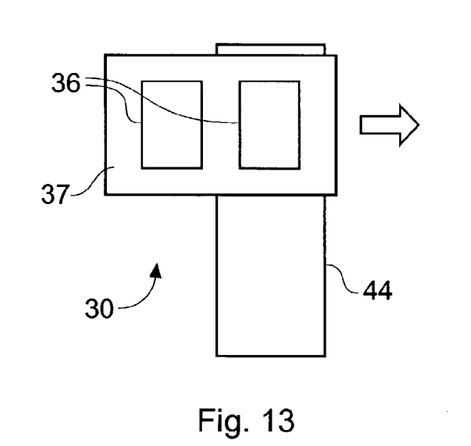
FIG. 13 shows an alternative washing/drying station.

FIG. 13 shows an alternative embodiment of washing and drying station 30. The design is essentially the same as the main embodiment, but the park station is no longer static, but provided with a lateral drive for moving the park station relative to the drying station in a direction at right angles to the drive direction of the wash station, as indicated in the figure with the arrow. The park station 37 is provided with first and second parking bays 36 and is movable between two positions, so as to arrange a pin head parked in either parking bay in readiness for washing or drying. The park station 37 is mounted so as to be drivable relative to the main frame 44 used to support the drying and washing stations. The advantage of this alternative embodiment is that the robot only needs to be provided with a single washing and drying station instead of two.

Although the main embodiment describes a process involving two pin heads, it will be appreciated that three or more pin heads could be used. A suitable number of parking bays would of course need to be provided, where the number of parking bays is preferably at least equal to the number of heads. If, for example, three pin heads were provided, the robot could be fitted with three washing/drying stations, one for each pin head, two washing/drying stations, or a single shared washing/drying station.

It will also be appreciated that alternative designs of the wash station are possible. The design of the main embodiment is but one possibility. For example, the washing process need not be based on liquid circulation channels, but could involve directly spraying the pins with water jets, and/or could incorporate a brushing action using brushes.

For colony picking applications, it will be appreciated that as well as multiple pin heads for performing the picking, it will often be useful to provide a liquid handling head for filling of well plates with a buffer solution, a master mix etc. in preparation for picking. A gel coring head or any other head type could also be fitted if desired.

What is claimed is:

1. An automated spotting or picking process using a robot that comprises a single xyz positioning apparatus comprising x- y- and z-positioners for moving a head attached to it around the robot, wherein heads can be clamped to and released from the xyz positioning apparatus in an automated manner by an attachment mechanism, the process comprising the steps of:
   (a) performing spotting or picking using a first pin head attached to the xyz positioning apparatus;
   (b) depositing the first pin head from the xyz positioning apparatus into a parking bay of an automated washing and drying apparatus for it to be cleaned in the automated washing and drying apparatus without involvement of the xyz positioning apparatus;
   (c) cleaning the first pin head in the automated washing and drying apparatus without involvement of the xyz positioning apparatus;
   (d) picking up a second pin head that is clean with the xyz positioning apparatus;
   (e) performing spotting or picking with the second pin head attached to the xyz positioning apparatus;
   (f) depositing the second pin head from the xyz positioning apparatus into the parking bay of the automated washing and drying apparatus for it to be cleaned in the automated washing and drying apparatus without the involvement of the xyz positioning apparatus;
   (g) cleaning the second pin head in the automated washing and drying apparatus without involvement of the xyz positioning apparatus;
   (h) picking up the first pin head that has been cleaned in the automated washing and drying apparatus with the xyz positioning apparatus;
   (i) performing spotting or picking with the first pin head attached to the xyz positioning apparatus; and
   (j) repeatedly carrying out (b) to (i).

2. The process of claim 1, wherein the automated washing and drying apparatus comprises a first automated washing and drying station and a second automated washing and drying station.

3. The process of claim 2, wherein each washing and drying station has a parking bay into which a pin head can be deposited.

4. The process of claim 2, wherein the first automated washing and drying station is used for washing and drying the first pin head and the second automated washing and drying station is used for washing and drying the second pin head.

5. The process of claim 1, wherein the automated washing and drying apparatus comprises a single automated washing and drying station.

6. The process of claim 5, wherein the automated washing and drying station comprises first and second parking bays in which pin heads can be deposited, and a drive for shuttling between them so that a pin head in either parking bay can be washed and dried.

7. The process of claim 5, wherein the automated washing and drying station comprises a parking bay, and the robot has at least first and second further parking bays, and is programmed so that the positioning apparatus can swap a dirty pin head for a clean pin head to perform steps (b) and (d) or (f) and (h) by:
   (i) depositing the dirty pin head in the first further parking bay;
   (ii) picking up the clean pin head from the washing and drying station and depositing it in the second further parking bay;
   (iii) picking up the dirty pin head from the first further parking bay and depositing it in the parking bay of the automated washing an drying station; and
   (iv) picking up the clean pin head from the second further parking bay.

* * * * *